United States Patent [19]

Letts

[11] Patent Number: 4,739,122
[45] Date of Patent: Apr. 19, 1988

[54] PREPARATION OF KETONES

[75] Inventor: John B. Letts, Charleston, W. Va.

[73] Assignee: Union Carbide Corporation, Danbury, Conn.

[21] Appl. No.: 788,930

[22] Filed: Oct. 18, 1985

[51] Int. Cl.⁴ .............................................. C07C 45/45
[52] U.S. Cl. ..................................... 568/388; 568/390; 568/391; 568/396; 568/406; 568/403
[58] Field of Search ............... 568/388, 390, 391, 403, 568/406, 396

[56] References Cited

U.S. PATENT DOCUMENTS

| | | | |
|---|---|---|---|
| 2,064,254 | 12/1936 | Fuchs et al. | 568/391 |
| 2,697,730 | 12/1954 | Mecorney et al. | 568/391 |
| 2,725,400 | 11/1955 | Mercorney et al. | |
| 2,879,298 | 3/1959 | Seligman | 568/388 |
| 3,316,303 | 4/1967 | Merlzweiller et al. | 568/390 |
| 3,657,351 | 4/1972 | Araki et al. | 568/391 |
| 3,701,798 | 10/1972 | Snapp et al. | 568/390 |
| 3,890,390 | 6/1975 | Aprahamian et al. | 260/590 |
| 3,966,822 | 6/1976 | Fukui et al. | 260/593 R |
| 4,146,581 | 3/1979 | Nissen et al. | 568/390 |
| 4,270,006 | 5/1981 | Heilen et al. | 568/388 |

FOREIGN PATENT DOCUMENTS 1310614 3/1973 United Kingdom .
1194058 6/1976 United Kingdom .

OTHER PUBLICATIONS

J. Org. Chem., 7, 189–198 (1942), V. N. Ipatieff et al.
Enc. of Chem Tech., 13, 894–940, John Wiley, NYC (1981) Kirk–Othmer.

Primary Examiner—James H. Reamer

[57] ABSTRACT

A process to produce Methyl Amyl Ketone heterogeneously via the cross-aldol condensation reaction between a $C_3$ (isopropanol or acetone feed) and a $C_4$ (butanol or butyraldehyde feed). The catalyst, hydrogen reduced copper oxide on gamma alumina, produces both high reactivity and long catalyst lifetimes. The catalyst is successfully regenerated. Efficiencies to MAK range from 50 to 80 wt. % and efficiencies to useful products range from 75 to 95 wt. % depending on the composition of the feed and temperature. Temperatures range from 200° to 262° C.

In general, this catalyst readily catalyzes the cross-aldol condensation reaction between aldehydes (or primary alcohols) and ketones (or secondary alcohols) to produce higher molecular weight ketones; likewise, this catalyst catalyzes the aldol condensation reaction between the same or different ketones to again produce higher molecular weight ketones.

25 Claims, No Drawings

PREPARATION OF KETONES

BACKGROUND OF THE INVENTION

1. Field of the Invention

This invention pertains to the preparation of higher molecular weight aliphatic ketones and more particularly to the catalytic cross-aldol condensation of aldehydes or primary alcohols and ketones or secondary alcohols. The catalyst also catalyzes the aldol condensation of the same or different ketones to produce higher molecular weight ketones.

2. Prior Art

A general review on the technology applicable to the manufacturing a higher molecular weight ketones is found in the article [Ketones by A. J. Papa and P. D. Sherman, Jr., in the third edition, Volume 13, pages 894–941 of Kirk-Othmer: Encyclopedia of Chemical Technology (John wiley and Sons, Inc.).

U.S. Pat. No. 3,890,390 describes the non-catalytic coupling of olefins such as 1-butene to acetone to give methyl ketones such as MAK at elevated temperatures (300° to 650° C.) and pressures (300 to 1500 psi). This process is energy intensive.

Zirconium on various supports is utilized most usefully at temperatures greater than 300° C. to produce higher molecular weight ketones via decarboxylation of aldehydes or their mixtures (U.S. Pat. No. 3,966,822). In a similar process U.S. Pat. No. 1,194,058 teaches that a saturated aliphatic aldehyde and a saturated monocarboxylic acid can react in the vapor phase over a manganese oxide on alumina catalyst to produce higher molecular weight ketones.

Ipatieff [J. Org. Chem., 7, 189–98 (1942)] has shown that copper-alumina and copper-zinc oxide alumina are simultaneously active for dehydrogenation and dehydration. The alcohols used are primary and secondary alcohols. In the case of the primary alcohols it is necessary to work at temperatures of the order of 300° to 350° C.

GB Pat. No. 1,310,614 divulges that a solid catalyst containing copper, chromium, and metal oxides such as barium, calcium, or zinc catalyze the conversion of ketones or aldehydes to higher molecular weight carbonyl compounds. However, alcohols cannot be fed.

Finally, U.S. Pat. No. 2,725,400 uses copper on alumina as well as copper on zinc alumina to catalyze the conversion of alcohols and/or ketones to higher molecular weight ketones. The preferred catalyst is a copper on zinc alumina; whereas, the preferred feed is secondary alcohols as well as ketones derived from them. Relatively high temperatures (greater than 240° C.) and pressures (greater than 175 psi) are required to operate under their conditions.

Methyl Amyl Ketone (MAK), a linear, $C_7$ ketone, is a high solids coating solvent which has a projected high growth potential by the late 1980's and beyond. A high solids coating solvent allows more resin or polymer to be dissolved/suspended in the solvent. Economic and environmental concerns dictate that the resin to solvent ratio be as high as possible. MAK has the right coating properties and can absorb large amounts of resin/polymer which means smaller amounts of solvent are introduced into the atmosphere and the coating industry uses correspondingly smaller amounts of solvent. MAK is a valued, commercial coating solvent.

It is an object of this invention to provide a method for preparing higher molecular weight ketones.

It is a further object of this invention to provide a facile and economical method for preparing methyl amyl ketone.

Other objects will become apparent to those skilled in the art upon a further reading of the specification.

SUMMARY OF THE INVENTION

A process for preparing higher molecular weight ketones has been discovered which comprises contacting at least one of the following:

(a) ketones having the generic formula:

wherein $R_1$ and $R_2$ are each linear or branched alkyls having 1 to about 10 carbons; and/or (b) secondary alcohols having the generic formula:

wherein $R_1$ and $R_2$ are as defined above, (c) aldehydes having the generic formula:

(d) primary alcohols having the generic formula:

wherein $R_3$ is a linear or branched alkyl having 1 to about 10 carbons, with a catalyst consisting essentially of a metal selected from the class consisting of copper, palladium, chromium and cobalt, or mixtures thereof, deposited on an acidic catalyst support, at a temperature of about 180° C. to about 350° C. at a LSHV (linear hourly space velocity) of about 0.1 to about 10 at a pressure up to about 300 psig.

DESCRIPTION OF THE INVENTION

Exemplary ketones useful in the practice of this invention include: acetone, methyl ethyl ketone, methyl propyl ketone, methyl isobutyl ketone, 2-heptanone and the like.

Representative secondary alcohols that can be used in this invention include: isopropanol, isobutanol, 2-butanol, and the like.

Aldehydes which can be used in this invention include: formaldehyde, acetaldehyde, propionaldehyde, butyraldehyde, isobutyraldehyde, heptanal, decanal, and the like.

Primary alcohols useful in this invention are: methanol, ethanol, n-propanol, butanol, 1-pentanol, 1-heptanol, 1-octanol, 1-nonanol, 1-decanol, and the like.

The ratio of secondary alcohols or ketones to primary alcohols or aldehydes is not narrowly critical and can vary from about 100:1 to about 4:1 by weight. A preferred ratio is between about 50:1 to about 4:1. A more preferred ratio is about 20:1 to about 4:1.

Both secondary alcohols and ketones can be used at the same time and the ratio of one to the other is not narrowly critical. When used together a preferred ratio of secondary alcohols to ketones is about 10:1, to about 1:10 by weight, with a most preferred ratio being between about 5:1 and about 1:5.

Likewise, the ratio of primary alcohols to aldehydes is not narrowly critical and can vary between about 10:1 and about 1:10 by weight with the most preferred ratio being about 5:1 to about 1:1.

Although temperatures of about 180° C. to about 320° C. can be used in the claimed invention, it is preferred to use a range of about 200° C. to about 280° C. with a range of about 210° C. to about 270° C. being most preferred.

Pressure is also not narrowly critical but for reasons of economy it is preferred to use pressure in the range of atmospheric up to about 300 psig. A preferred range is between atmospheric and 100 psig with a range of between atmospheric and 60 psig being most preferred. However, at higher pressures care must be taken to consider the dew points of the reactants and the products which depend on temperature and pressure.

If the total alcohol content of the reactants fed to the catalyst reaction zone falls below about 30 percent by weight, hydrogen must be added to the reaction. Alcohols such as isopropanol and butanol readily undergo dehydrogenation under the reaction conditions of this invention to produce hydrogen which is utilized in the production of higher molecular weight ketones. When hydrogen is added the hydrogen flow can vary between 0.1 liters/1 hour and 10 liters/1 hour with a range of about 0.5 being preferred.

The water content of the feed can vary between zero and about 20 percent by weight.

Any combination of reactants can be used. Thus for example all primary alcohols and/or aldehydes or all secondary alcohols or ketones can be used.

There is a wide range of products that can be obtained with this technology. For example, isopropanol (or acetone) can combine with butanol (or butyraldehyde) to give MAK. The nonrestrictive list of other ketones that can be produced include methyl ethyl ketone, methyl isobutyl ketone, methyl isopropyl ketone, methyl butyl ketone, 2-methyl-4-heptanone, and 4-methyl-2-heptanone. Suffice it to say that the products are the arithmetic sum of the number of carbon atoms in the combined reactants. For example, a three carbon primary alcohol reacts with a four carbon secondary alcohol to give a seven carbon ketone or a two carbon primary alcohol reacts with a three carbon secondary alcohol to give a five carbon ketone.

The catalyst in this invention consists of a metal or metals on an acidic support. A variety of metals can be used including, but not exclusive of, copper, palladium, chromium and cobalt. The more preferred catalysts is copper. Furthermore, combinations of these metals are effective catalysts. Most notable among the combinations is copper and chromium. The percent by weight of metals on the support can vary between 0.1 percent and 95 percent, more preferably between 1 percent and 50 percent, and most preferable between 5 and 20 percent. In combinations of metals the molar ratios can vary extensively. For example, in the bimetallic combination, copper and chromium, the copper to chromium ratio can vary from 1000:1 to 1:100, more preferably from 100:1 to 1:10, and most preferably from 20:1 to 1:1.

The support utilized in this invention is generally of high surface area and activity and is relatively acidic. In general an acidic support is required when primary alcohols—in other words aldehydes—undergo aldol condensation reactions with themselves or with ketones. Basic supports, which incorporate such metals as calcium and zinc, react with acids in the product thereby deactivating the catalyst. Acids originate from the hydration of esters via the Tischenko reaction. The formation of esters via the Tischenko reaction involves the reaction of two aldehydes with loss of a mole of hydrogen. Equations 5-7 illustrate the formation of acids from aldehydes. The supports used in this invention are:

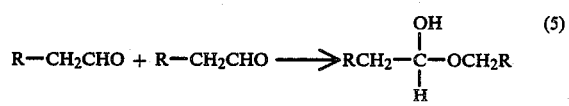

$$R-CH_2CHO + R-CH_2CHO \longrightarrow RCH_2-\underset{\underset{H}{|}}{\overset{\overset{OH}{|}}{C}}-OCH_2R \quad (5)$$

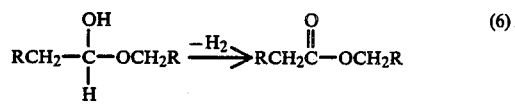

$$RCH_2-\underset{\underset{H}{|}}{\overset{\overset{OH}{|}}{C}}-OCH_2R \xrightarrow{-H_2} RCH_2\overset{\overset{O}{\|}}{C}-OCH_2R \quad (6)$$

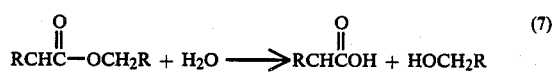

$$R\overset{\overset{O}{\|}}{CHC}-OCH_2R + H_2O \longrightarrow R\overset{\overset{O}{\|}}{CHCOH} + HOCH_2R \quad (7)$$

relatively acidic; their identities are well known to those of ordinary skill in this art. Typical examples include, but are not limited to, gamma alumina, silica, and zirconium phosphate. A very useful support is gamma alumina.

The catalyst can be made into a variety of shapes including, but not exclusive of, pellets, tablets and extrusions. The size of the catalyst can vary from 1/16" to over 1" in diameter. The most preferred size is between ⅛" and 5/16".

Although most of the catalysts can be purchased commercially, they can also be prepared. The art of preparation of these catalysts is known to those of ordinary skill.

The resulting higher molecular weight ketones produced, for example MAK, can be refined by conventional refining methods.

The general chemistry utilized for the reaction of primary alcohols with secondary alcohols in this invention is shown below (Scheme 1).

The present invention provides a process whereby higher molecular weight ketones are produced by feeding alcohols, aldehydes or ketones or mixtures thereof over a reduced copper oxide on gamma alumina catalyst at relatively low temperatures and pressures. As an example, this invention describes the conversion of a $C_3$ compound (isopropanol or acetone) and a $C_4$ compound (butanol or butyraldehyde) and optionally hydrogen to MAK.

Previous workers had indicated that primary alcohols (aldehydes) either were not the preferred feed (in other words relatively unreactive) or required temperatures in excess of 300° C. The problem centers around the use of basic oxides such as zinc with alumina which reacts gradually with primary alcohols thereby deactivating the catalyst.

Besides utilizing appropriate catalysts such as reduced copper oxide on gamma alumina, this invention incorporates relatively low temperatures (200° to 270° C.) and pressures (14 to 100 psig) with feeding the proper ratio of primary alcohols (aldehydes) to secondary alcohols (ketones) to obtain the desired higher molecular weight ketones at high rates and efficiencies while maintaining moderate conversions. Under these conditions the catalyst can operate for thousands of hours before regeneration while feeding primary alcohols. In fact, the preferred feed includes both primary and secondary alcohols.

Furthermore, another important aspect of this invention is that the feed can be either wet or dry with no deleterious effects. This allows the use of the relatively cheap wet alcohols, aldehydes, and ketones such as constant boiling mixture isopropanol (88 percent isopropanol and 12 percent water). Upwards of 10 wt. % water has been incorporated into the feed.

A significant advantage of this invention is that higher molecular weight ketones such as MAK can be produced in one pass over the catalyst. The classical method of producing MAK, for example, requires as many as four individual steps (Equation 1-4). Admittedly, by feeding acetone and butyraldehyde and by vaporizing the aldol product:

$$CH_3CHOHCH_3 \xrightarrow{-H_2} CH_3COCH_3 \quad (1)$$

$$CH_3CH_2CH_2OH \xrightarrow{-H_2} CH_3CH_2CH_2CHO$$

$$\begin{matrix} CH_3COCH_3 \\ CH_3CH_2CH_2CHO \end{matrix} \Big\rangle \rightarrow CH_3COCH_2CHOHCH_2CH_2CH_3 \quad (2)$$

$$CH_3COCH_2CHOHCH_2CH_2CH_3 \xrightarrow{-H_2O} \quad (3)$$

$$CH_3COCH=CHCH_2CH_2CH_3$$

$$CH_3COCH=CHCH_2CH_2CH_3 \xrightarrow{H_2} \quad (4)$$

$$CH_3COCH_2CH_2CH_2CH_2CH_3$$

in equation 2, thereby dehydrating it, two out of the four steps can be eliminated; however, the simplicity, ease, and flexibility of having four different reactions going on simultaneously on the catalyst surface cannot be over emphasized.

Scheme 1

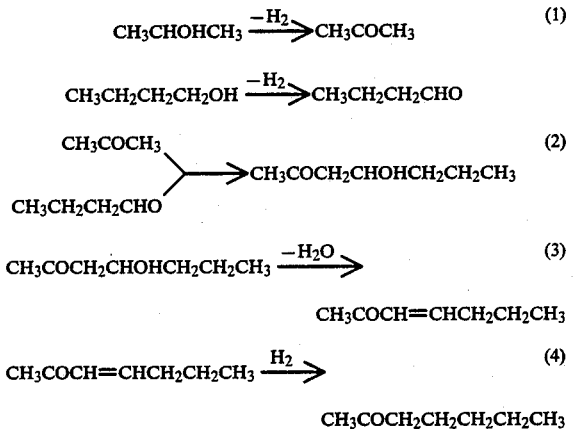

More specifically this chemistry is illustrated for the production of MAK from isopropanol and butanol (Scheme 2).

Scheme 2

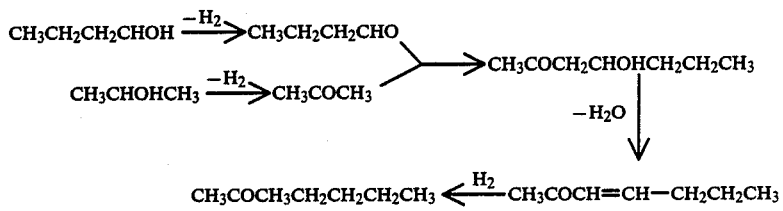

In general, this invention describes the process of producing higher molecular weight ketones from secondary alcohols (or ketones) and especially primary alcohols (or aldehydes) by judicious selection of catalysts, feed compositions, and relatively low temperatures and pressure to obtain high rates, efficiencies, and conversions and prolonged catalyst life.

The invention is further described in the examples which follow. All parts and percentages are by weight unless otherwise specified.

General Experimental Procedure

The equipment used in a standard experiment was a tubular reactor ½" I.D.×31" long heated by a "clamshell" furnace and operated 24 hours per day. The catalyst bed was 19 cc beneath a layer of glass beads used to vaporize the liquid feed. The tube was positioned so that the catalyst was in the center of the furnace.

The liquid feed was fed from a tank using a Milton Roy pump. The liquid was pumped to the top of the tube and passed down through the catalyst. The product passed through a cold condenser and was collected in a receiver which had a cold trap connected between the receiver and the vent system.

The product was analyzed by gas chromatography on a Varian 3700 equipped with an auto sampler on a DB1701-30w fused silica capillary column. Compounds were recorded as weight percent as determined by response factors for each component found in a standard reference mixture.

Water content was obtained using a Mettler memotitrator (Karl-Fisher method).

Total weight percent acidity was calculated by using the standard acid-base titration method with 0.1 alcoholic potassium hydroxide as the base.

The definition of MAK efficiency is: weight percent MAK divided by weight percent of reactants in minus weight percent of reactants out minus weight percent water found. Efficiency to useful products is the same as MAK efficiency except that the weight percent MAK is replaced by the weight percent of all useful products found.

TABLE 1

| Example | 1 | 2 | 3 | 4 | 5 | 6 | 7 | 8 |
|---|---|---|---|---|---|---|---|---|
| Lights | 0.0 | trace | 0.1 | 0.0 | 0.1 | trace | 0.1 | 0.1 |
| Acetone | 69.5 | 69.2 | 66.7 | 54.2 | 53.3 | 53.5 | 59.4 | 64.7 |
| Isopropanol | 1.1 | trace | trace | 13.6 | 5.8 | 7.6 | 9.9 | 12.3 |
| Butyraldehyde | 5.9 | 5.3 | 3.1 | 1.5 | 1.6 | 2.8 | 0.9 | 0.2 |
| Butanol | 4.1 | 2.3 | 0.7 | 10.2 | 3.7 | 6.2 | 2.1 | 0.7 |
| MIBK* | 0.3 | 0.4 | 0.6 | 1.1 | 1.5 | 0.6 | 1.1 | 2.0 |
| MAK* | 12.2 | 14.6 | 18.1 | 11.3 | 18.3 | 12.7 | 10.6 | 5.9 |
| EHA* | 0.4 | 0.2 | trace | 0.0 | 0.0 | 0.0 | 0.0 | 0.0 |
| BuBu* | 1.8 | 1.9 | 0.6 | 0.8 | 0.7 | 0.7 | trace | 0.0 |
| DAK* | 2.3 | 3.1 | 6.3 | 2.1 | 7.6 | 2.6 | 1.8 | 0.5 |
| Unknowns | 0.0 | trace | 0.5 | 2.8 | 3.9 | 1.4 | 2.1 | 2.1 |

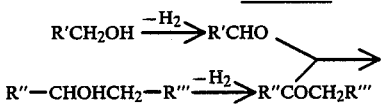

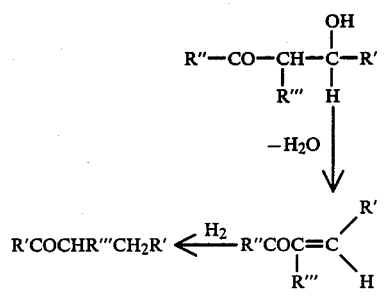

TABLE 1-continued

| Example | 1 | 2 | 3 | 4 | 5 | 6 | 7 | 8 |
|---|---|---|---|---|---|---|---|---|
| $H_2O$ | 2.5 | 3.0 | 3.5 | 2.5 | 3.5 | 12.0 | 12.0 | 11.5 |

*MIBK = Methyl isobutyl Ketone
MAK = Methyl Amyl Ketone
EHA = Ethyl Hexaldehyde
BuBu = Butyl Butyrate
DAK = Diamyl Ketone

EXAMPLE 1

To a tubular reactor was added 19 cc of 12% copper oxide on gamma alumina. The tube was purged with nitrogen for three hours then the catalyst was heated to 121° C. under a nitrogen flow for one hour. The nitrogen was replaced with 5% hydrogen in nitrogen and heated for one hour at 121° C. The temperature was then raised to 176° C. and held there for one hour. Then the temperature was raised to 204° C. and held there for sixteen hours. Next the 5% hydrogen in nitrogen was shut off and the reactor was purged with nitrogen for several hours. In this case, the hydrogen valve was open and a flow of one liter per hour was established at atmospheric pressure. The temperature was then raised to 217° C. Subsequently, a feed of 20% butyraldehyde and 80% acetone was established at a linear hourly space velocity (LHSV) of 0.98 cc of feed per cc of catalyst per hour. The major product, MAK, is 12.2% of the product. See Table 1 for a complete list of products. Unreacted acetone and butyraldehyde along with isopropanol and butanol can be recycled back to the reactor. The efficiency to MAK is 72.0%. The efficiency to useful products (MAK, MIBK, EHA, and DAK) is 89.3%. The conversion of acetone is 11.8%. The conversion of butyraldehyde is 50.8%.

EXAMPLE 2

Example 1 was repeated with the exception that the temperature is raised to 239° C. The major product is MAK at 14.6%. The efficiency to MAK is 72.0%. The efficiency to useful products is 90.3%. The conversion of acetone is 13.5%. The conversion of butyraldehyde is 62.4%. See Table 1 for a complete list of products.

EXAMPLE 3

Example 1 was repeated with the exception that the temperature was raised to 253° C. and the LHSV was slightly lower (0.93). The major product was again MAK (18.0%). The efficiency to MAK is 69.2%. The efficiency to useful products is 95.5%. The conversion of acetone is 16.6%. The conversion of butyraldehyde is 81.4%. See Table 1 for a complete list of products.

EXAMPLE 4

Example 1 was repeated with the exception that the feed is 40% acetone, 40% isopropanol, and 20% butanol, no hydrogen is added to the feed, and the temperature is 216° C. The LHSV is 0.98. The major product is MAK (11.3%). The efficiency to MAK is 62.4%. The efficiency to useful product is 80.1%. The conversion of isopropanol is 14.6%*. The conversion of butanol is 41.4%**. See Table 1 for a complete list of products.

*Total $C_3$ conversion is based on isopropanol with a correction for loss of hydrogen in acetone.
**Butanol conversion takes into account the presence of butyraldehyde in the product with the necessary correction for hydrogen loss.

EXAMPLE 5

Example 4 was repeated with the exception that the temperature was raised to 252° C. The major product is MAK (18.3%). The efficiency to MAK is 56.9%. The efficiency to useful products is 85.3%. The conversion of isopropanol is 25.5%. The converson of butanol is 73.2%. See Table 1 for a complete list of products.

EXAMPLE 6

Example 4 was repeated with the exception that the feed was changed to 35% acetone, 37.5% isopropanol, 17.5% butanol, and 10% water and the temperature is 249° C. The major product is MAK (12.7%). The efficiency to MAK is 73.4%. The efficiency to useful products is 91.9%. The conversion of isopropanol is 14.8%. The conversion of butanol is 48.3%. See Table 1 for a complete list of products.

EXAMPLE 7

Example 4 was repeated with the exception that the feed is 40% acetone, 40% isopropanol, 10% butanol, and 10% water, and the temperature is 254° C. The major product is MAK (10.6%). The efficiency to MAK is 67.4%. The efficiency is useful product is 80.5%. The conversion of isopropanol is 12.5%. The conversion of butanol is 85.2%. See Table 1 for a complete list of products.

EXAMPLE 8

Example 4 was repeated with the exception that the feed is 40% acetone, 45% isopropanol, 5% butanol, and 10% water, and the temperature is 251° C. The major product is MAK (5.9%). The efficiency to MAK is 55.5%. The efficiency to useful products is 79.2%. The conversion of isopropanol is 8.4%. The conversion of butanol is 80.6%.

Although the invention has been described in its preferred forms with a certain degree of particularly, it is understood that the present disclosure has been made only by way of example and that numerous changes can be made without departing from the spirit and the scope of the invention.

I claim:

1. Process for preparing higher molecular ketones consisting of contacting at least one keton having the generic formula:

$$R_1-CO-R_2$$

wherein $R_1$ and $R_2$ each is a linear or branched alkyl having 1 to about 10 carbons, optionally in the presence of hydrogen and/or water, with a catalyst consisting essentially of a metal and/or metal oxide selected from the class consisting of copper, palladium, chromium, copper oxide, a mixture of at least any two of copper, copper oxide, palladium and chromium, a mixture of cobalt and copper, a mixture of cobalt and palladium, a mixture of cobalt and copper oxide, and a mixture of cobalt and chromium, deposited on an acidic catalyst support, said process being conducted at a temperature in the range of about 180° to about 350°, at a LHSV of about 0.1 to about 10 and at a pressure of up to about 300 psig.

2. Process as claimed in claim 1 wherein the ketone is acetone.

3. Process as claimed in claim 1 wherein the temperature is about 210° to about 280° C., the pressure is about 14 to 100 psig, and the LHSV is about 0.5 to about 1.5.

4. Process as claimed in claim 1 wherein the support is gamma-alumina or silica.

5. Process for preparing higher molecular ketones consisting of contacting
(a) at least one ketone having the generic formula:

$$R_1-CO-R_2$$

wherein $R_1$ and $R_2$ each is a linear or branched alkyl having 1 to about 10 carbon atoms, and at least one of the following:
(b) at least one secondary alcohol having the generic formula:

$$R_1-CHOH-R_2$$

wherein $R_1$ and $R_2$ are as defined above, and
(c) at least one primary alcohol having the generic formula:

$$R_3-CH_2OH$$

wherein $R_3$ is a linear or branched alkyl having 1 to about 10 carbons, optionally in the presence of hydrogen and/or water, with a catalyst consisting essentially of a metal and/or metal oxide selected from the group consisting of palladium, and a mixture of palladium and at least one of copper, copper oxide, chromium and cobalt, deposited on an acidic catalyst support, said process being conducted at a temperature in the range of about 180° to 350° C., at a LHSV of about 0.1 to about 10 and at a pressure of up to about 300 psig.

6. Process as claimed in claim 5 wherein the temperature is about 210° to about 280° C., the pressure is about 14 to 100 psig, and the LHSV is about 0.5 to about 1.5.

7. Process as claimed in claim 5 wherein the support is gamma-alumina or silica.

8. Process for preparing higher molecular ketones consisting of contacting at least one secondary alcohol having the generic formula:

$$R_1-CHOH-R_2$$

wherein $R_1$ and $R_2$ each is a linear or branched alkyl having 1 to about 10 carbons, optionally in the presence of hydrogen and/or water, with a catalyst consisting essentially of a metal and/or metal oxide selected from the class consisting of copper, copper oxide, palladium, chromium, cobalt, and a mixture of at least any two of said metals and/or metal oxide, deposited on an acidic catalyst support, said process being conducted at a temperature in the range of about 180° to about 350° C., at a LHSV of about 0.1 to about 10 and at a pressure of up to about 300 psig.

9. Process as claimed in claim 8 wherein the temperature is about 210° to about 280° C., the pressure is about 14 to 100 psig, and the LHSV is about 0.5 to about 1.5.

10. Process as claimed in claim 8 wherein the support is gamma-alumina or silica.

11. Process for preparing higher molecular ketones consisting of contacting:
(a) at least one secondary alcohol having the generic formula:

$$R_1-CHOH-R_2$$

wherein $R_1$ and $R_2$ each is a linear or branched alkyl having 1 to about 10 carbon atoms, and at least one of the following:
(b) at least one primary alcohol having the generic formula:

$$R_3-CH_2OH$$

wherein $R_3$ is a linear or branched alkyl having 1 to about 10 carbons, and
(c) at least one aldehyde having the generic formula:

$$R_3-CHO$$

wherein $R_3$ is defined as above, optionally in the presence of hydrogen and/or water, with a catalyst consisting essentially of a metal and/or metal oxide selected from the class consisting of copper, copper oxide, palladium, chromium, cobalt, and a mixture of at least any two of said metals and/or metal oxide, deposited on an acidic catalyst support, said process being conducted at a temperature in the range of about 180° to about 350° C., at a LHSV of about 0.1 to about 10 and at a pressure of up to about 300 psig.

12. Process as claimed in claim 11 wherein the temperature is about 210° to about 280° C., the pressure is about 14 to 100 psig, and the LHSV is about 0.5 to about 1.5.

13. Process as claimed in claim 11 wherein the support is gamma-alumina or silica.

14. Process for preparing higher molecular ketones consisting of contacting at least one primary alcohol having the generic formula:

$$R_3-CH_2OH$$

wherein $R_3$ is a linear or branched alkyl having 1 to about 10 carbons, optionally in the presence of hydrogen and/or water, with a catalyst consisting essentially of a metal and/or metal oxide selected from the class consisting of copper, copper oxide, palladium, chromium, cobalt, and a mixture of at least any two of said metals and/or metal oxide, deposited on an acidic catalyst support, said process being conducted at a temperature in the range of about 180° to about 350° C., at a LHSV of about 0.1 to about 10 and at a pressure of up to about 300 psig.

15. Process as claimed in claim 14 wherein the primary alcohol is ethanol.

16. Process as claimed in claim 14 wherein the temperature is about 210° to about 280° C., the pressure is about 14 to 100 psig, and the LHSV is about 0.5 to about 1.5.

17. Process as claimed in claim 14 wherein the support is gamma-alumina or silica.

18. A process for preparing higher molecular ketones consisting of contacting
(a) at least one primary alcohol having the generic formula:

$$R_3-CH_2OH$$

wherein $R_3$ is a linear or branched alkyl having 1 to about 10 carbons, and
(b) at least one aldehyde having the generic formula:

$$R_3-CHO$$

wherein $R_3$ is as defined above, optionally in the presence of hydrogen and/or water, with a catalyst consisting essentially of a metal and/or metal oxide selected from the class consisting of copper, copper oxide, palladium, chromium, cobalt, and a mixture of at least any two of said metals and/or metal oxide, deposited on an acidic catalyst support, said process being conducted at a temperature in the range of about 180° to about 350° C., at a LHSV of about 0.1 to about 10 and at a pressure of up to about 300 psig.

19. Process as claimed in claim 18 wherein the aldehyde is butyraldehyde and the primary alcohol is ethanol.

20. Process as claimed in claim 18 wherein the temperature is about 210° to about 280° C., the pressure is about 14 to 100 psig, and the LHSV is about 0.5 to about 1.5.

21. Process as claimed in claim 18 wherein the support is gamma-alumina or silica.

22. Process for preparing higher molecular ketones consisting of contacting at least one aldehyde having the generic formula:

$$R_3-CHO$$

wherein $R_3$ is a linear or branched alkyl having 1 to about 10 carbons, optionally in the presence of hydrogen and/or water, with a catalyst consisting essentially of a metal and/or metal oxide selected from the class consisting of copper, copper oxide, palladium, chromium, cobalt, and a mixture of at least any two of said metals and/or metal oxide, deposited on an acidic catalyst support, said process being conducted at a temperature in the range of about 180° to about 350° C., at a LHSV of about 0.1 to about 10 and at a pressure of up to about 300 psig.

23. Process as claimed in claim 22 wherein the aldehyde is butyraldehyde.

24. Process as claimed in claim 22 wherein the temperature is about 210° to about 280° C., the pressure is about 14 to 100 psig, and the LHSV is about 0.5 to about 1.5.

25. Process as claimed in claim 22 wherein the support is gamma-alumina or silica.

* * * * *